United States Patent [19]
Liprie

[11] Patent Number: 5,947,924
[45] Date of Patent: Sep. 7, 1999

[54] DILATATION/CENTERING CATHETER USED FOR THE TREATMENT OF STENOSIS OR OTHER CONSTRICTION IN A BODILY PASSAGEWAY AND METHOD THEREOF

[75] Inventor: Samuel F. Liprie, Lake Charles, La.

[73] Assignee: Angiorad, L.L.C., Lake Charles, La.

[21] Appl. No.: 08/713,696

[22] Filed: Sep. 13, 1996

[51] Int. Cl.⁶ .................................................. A61M 29/00
[52] U.S. Cl. ............................................. 604/96; 606/194
[58] Field of Search ...................... 604/96–102; 606/192, 606/194; 600/3–5

[56] References Cited

U.S. PATENT DOCUMENTS

| | | |
|---|---|---|
| 4,762,130 | 8/1988 | Fogarty et al. . |
| 4,834,724 | 5/1989 | Geiss et al. . |
| 4,861,520 | 8/1989 | van't Hooft et al. . |
| 4,873,983 | 10/1989 | Winters . |
| 4,883,459 | 11/1989 | Calderon ................................... 604/28 |
| 4,884,573 | 12/1989 | Wijay et al. . |
| 4,932,959 | 6/1990 | Horzewski et al. . |
| 5,040,543 | 8/1991 | Badera et al. . |
| 5,106,360 | 4/1992 | Ishiwara et al. . |
| 5,112,301 | 5/1992 | Fenton, Jr. et al. . |
| 5,158,553 | 10/1992 | Berry et al. . |
| 5,163,905 | 11/1992 | Don Michael . |
| 5,174,302 | 12/1992 | Palmer . |
| 5,199,939 | 4/1993 | Dake et al. . |
| 5,209,730 | 5/1993 | Sullivan . |
| 5,213,561 | 5/1993 | Weinstein et al. . |
| 5,215,527 | 6/1993 | Beck et al. . |
| 5,226,888 | 7/1993 | Arney . |
| 5,256,150 | 10/1993 | Quiachon et al. . |
| 5,295,959 | 3/1994 | Gurbel et al. . |
| 5,295,960 | 3/1994 | Aliahmad et al. . |
| 5,302,168 | 4/1994 | Hess . |
| 5,308,356 | 5/1994 | Blackshear, Jr. et al. . |
| 5,312,344 | 5/1994 | Grinfeld et al. ........................ 604/101 |
| 5,318,587 | 6/1994 | Davey . |
| 5,354,257 | 10/1994 | Roubin et al. . |
| 5,383,856 | 1/1995 | Bersin . |
| 5,386,828 | 2/1995 | Owens et al. . |
| 5,395,333 | 3/1995 | Brill . |
| 5,397,307 | 3/1995 | Goodin . |
| 5,484,411 | 1/1996 | Inderbitzen et al. . |
| 5,503,613 | 4/1996 | Weinberger . |
| 5,540,659 | 7/1996 | Tierstein . |
| 5,554,119 | 9/1996 | Harrision et al. . |
| 5,599,306 | 2/1997 | Klein et al. .............................. 604/96 |
| 5,618,266 | 4/1997 | Liprie ...................................... 604/21 |
| 5,643,171 | 7/1997 | Bradshaw et al. . |

FOREIGN PATENT DOCUMENTS

| | | |
|---|---|---|
| 91 02 312 U | 6/1992 | Germany . |
| WO 9304735 | 3/1993 | WIPO . |
| WO 94/25106 | 11/1994 | WIPO . |
| WO9526681 | 10/1995 | WIPO . |
| WO 96/14898 | 5/1996 | WIPO . |

*Primary Examiner*—John D. Yasko
*Assistant Examiner*—Deborah Blyveis

[57] ABSTRACT

An apparatus and method for treating an occlusion or constriction, such as a stenosis in a blood vessel or other conduit in the body, as well as an apparatus and method for treating a tumor or cancerous area occurring around a conduit or duct in the body. The apparatus includes a catheter provided with a centering balloon including a catheter centering balloon encircling a portion of the catheter near its distal end. This centering balloon contains a plurality of thin spoke-like members. A second dilatation balloon attached to the surface of the catheter is used to treat the stenosed area. A radioactive source of material is included for treating the stenosis or cancer.

43 Claims, 3 Drawing Sheets

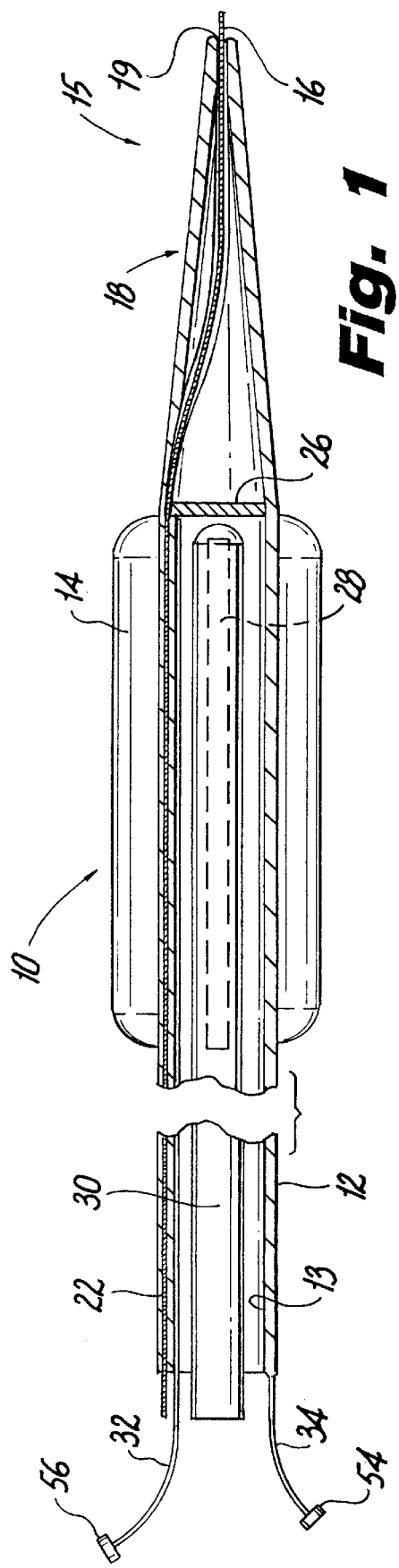
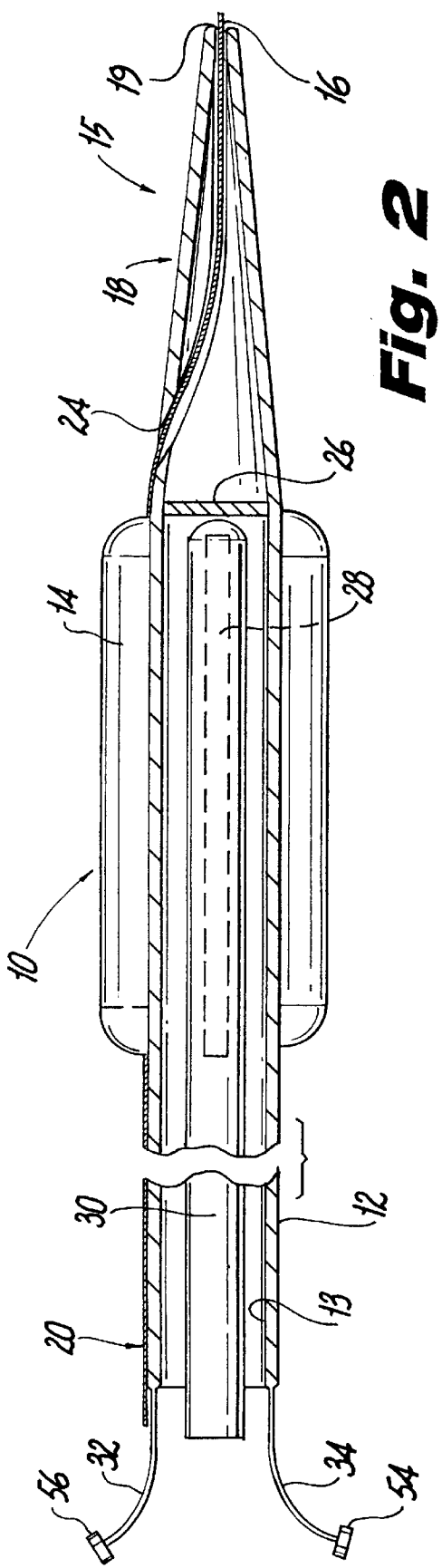

DILATATION/CENTERING CATHETER USED FOR THE TREATMENT OF STENOSIS OR OTHER CONSTRICTION IN A BODILY PASSAGEWAY AND METHOD THEREOF

BACKGROUND OF THE INVENTION

1. Field of the Invention

The present invention relates to the field of treating an occlusion or a constriction, such as a stenosis which would occur in various blood vessels and other bodily conduits as well as to the field of angioplasty. Additionally, the present invention is directed to the field of treating cancer which would occur in various body conduits or ducts, as well as to the field of brachytherapy.

2. Description of the Prior Art

Various techniques have been developed to treat many different conduits in the body when these conduits have become reduced in size due to the existence of a stenosis or have been completely occluded. These techniques include introducing a deflated balloon catheter to the site of an occlusion or constriction, such as a stenosis, inflating the balloon one or more times to eliminate the size of the stenosis, deflating the balloon and then removing the balloon catheter from the treatment site.

With respect to the vascular pathways, angioplasty is used to open an artery or blood vessel in the region where the stenosis or the occlusion has occurred. A typical angioplasty procedure consists of making a small incision through the body and into a blood vessel and then maneuvering a guide wire through the vascular system to a point beyond the stenosis or occlusion. A hollow catheter with a deflatable balloon near its distal end is threaded over the guide wire and advanced to the point of stenosis or occlusion. The balloon is then inflated and deflated several times to widen the constricted area, and is then withdrawn from the body.

Unfortunately, although the angioplasty procedure does markedly reduce the area of stenosis or occlusion, many patients exhibit a reoccurrence of the stenosis within a few months of the original procedure.

Although the original stenosis occurs by means of the build up of plaque over a relatively long period of time, experimentation has lead many to believe that the reoccurrence of the stenosis after the original angioplasty procedure is unrelated to the cause of the original stenosis. It is believed that the inflation of the balloon catheter used in the angioplasty procedure or the placement of a stent in the area of the stenosis causes irritation to the blood vessel. This irritation produces a mechanism of action called hyperplasia, inducing the inner layer of the blood vessel cells to rapidly reproduce, thereby causing restenosis. It has been proposed that if the blood vessel is irradiated at the point of the stenosis with a radioactive dose, the mechanism that causes hyperplasia would be destroyed without harming the blood vessel itself.

During this procedure, it is important to precisely control the amount of radiation which is directed to the blood vessel wall, since too much radiation could actually induce hyperplasia as well as destroying a portion of the blood vessel, making it possible for an aneurism or rupture to occur. U.S. Pat. No. 5,213,561 issued to Weinstein et al and U.S. Pat. No. 5,199,939 issued to Dake et al, as well as PCT Application PCT/US92/07447 to Shefer et al, describe various methods and apparatus for introducing radiation to the site of a stenosis to endeavor to prevent restenosis.

The Weinstein et al patent describes a method and apparatus for preventing restenosis after angioplasty. A balloon catheter transported by a conventional guide wire is delivered to the location of the stenosis. Particles or crystals of radioactive material are embedded or mounted on a tube provided inside the balloon catheter. A retractable radiation shielding sleeve is slidable along the tube to cover the source of radioactive material. Upon completion of the angioplasty, the shielding sleeve is retracted and the area of the stenosis is irradiated. Although this apparatus does introduce radiation to the point of the stenosis, the retractable shielding surrounding the source of radioactive material makes this catheter bulky and unwieldy to use. In this regard, it is very doubtful that a catheter system this bulky would fit into the smaller branches or vessels of the heart. It is also doubtful that a catheter this bulky and stiff could be maneuvered through the tighter bends and turns in many of the vessels.

An additional embodiment of the Weinstein et al patent illustrates a stent which is made of or coated with a radioactive material such as iridium 192. Since the radioactive material is provided on the outer surface of the stent, it is very difficult to precisely administer the proper dosage of radiation to prevent hyperplasia without administering a level of radiation which would actually induce hyperplasia or other deleterious effects to the blood vessel.

The PCT application illustrates a method and apparatus for restenosis treatment by applying a radioactive dose to the stenosed region after reduction of the region by angioplasty or other means. As shown in FIG. 4, an angioplasty balloon is expanded in the vicinity of a lesion site and radioactive elements provided on the exterior surface of the balloon are forced into contact with the region. Therefore, similar to the Weinstein et al patent, the presence of the radioactive material on the exterior of the catheter would make it very difficult to apply the precise amount of radiation to the region of interest. Additionally, both the PCT application as well as the patent to Weinstein describe balloon catheters which do not allow the blood within the vessel to flow during inflation of the balloon.

Although there have been some attempts to construct a dilatation balloon allowing for some perfusion of bodily fluids during the inflation phase of the dilatation, the perfusion is greatly diminished by the overall size of the inflated balloon. Dilatation balloons must be able to hold a great amount of pressure (up to 16 atmospheres) and must also be able to inflate to large overall diameters to open the stenosis areas inside the bodily conduits or narrow tortuous passageways. Both of these requirements lead to large, bulky dilatation balloons that encompass most, if not all, of the area inside the stenosed vessel leading to large blockages of bodily fluids and thus allowing for little, if any perfusion.

These types of balloons are described in U.S. Pat. Nos. 5,295,959, issued to Gurbel et al and 5,308,356, issued to Blackshear, Jr. et al. Both of these patents describe a passive perfusion dilatation catheter having a series of non-longitudinal lobes. As particularly illustrated in FIG. 1 of the Blackshear, Jr. et al patent, virtually the entire interior of the bodily conduit is blocked when the dilatation balloon is inflated, thereby preventing the flow of bodily fluids around the treatment site. Additionally, due to the particular structure of the balloons utilized, neither the Gurbel et al nor the Blackshear, Jr. et al balloon can be used to precisely center the catheter within the bodily conduit at the site of treatment.

Attempts to utilize these types of dilatation balloons as a centering balloon or treating the patient with radioactive materials would greatly compromise the patient for the many minutes while the treatment is being implemented due to the diminished flow of bodily fluids or, in some cases, the complete blockage of bodily fluids. Any compromises to the dilatation balloon to achieve a greater flow rate would greatly decrease the effectiveness of the balloon on the stenosed area.

Therefore, there exists a need for a balloon catheter system that will achieve the greatest amount of dilatation possible and would also allow for the centering of the treatment lumen inside the bodily conduit or passageway while allowing for the maximum flow rate of bodily fluids around the treatment site.

The patent to Dake et al shows a radioactive catheter for preventing restenosis after angioplasty. However, this patent merely indicates that an elongated flexible catheter is transported to the area of the original stenosis after a balloon catheter has been withdrawn, thereby lengthening the time to administer the entire procedure.

SUMMARY OF THE INVENTION

These and other deficiencies of the prior art are addressed by the present invention which is directed to a method and apparatus for treating the location of a stenosis in a blood vessel, or other hollow conduit or narrow tortuous passageway in the body. A radiopaque elongated, flexible guide wire is inserted into the body through a small incision and is then introduced into a blood vessel or similar conduit or passageway. Once in place, a catheter having a dilatation balloon (or series of balloons) and a centering balloon (or series of balloons) both attached near the distal end thereof is threaded over the guide wire and is also advanced to the location of treatment. The dilatation balloon or balloons is inflated and deflated one or more times to reduce the size of the stenosis. At this point, the centering balloon or balloons would be inflated. Since the centering balloons inflate symmetrically and are long with thin widths, they serve only to center the treatment lumen of the catheter inside the prior stenosed area while allowing for maximum bodily perfusion. A radioactive source or sources is advanced into position through the treatment lumen of the catheter to the site of the original stenosis. With the centering balloon or balloons inflated, the catheter and the radioactive source or sources are correctly centered within the bodily conduit or passageway to administer the precise dose to the original area of the stenosis. After a predetermined period of time has elapsed, the centering balloon or balloons are deflated and the radioactive source as well as the catheter and the guide wire are removed from the bodily conduit or passageway.

A second embodiment of the present invention would include a flexible membrane attached to either the dilatation balloon or the centering balloon to further insure that blood will be able to flow through the perfusion channels through each of the lobes of a multi-lobed dilatation balloon thereby assuring that plaque or other material would not clog these channels.

Finally, if the catheter is used to transport a source of radiation to the treatment site without the necessity of reducing the size of a stenosis, the dilatation balloon need not be attached to the catheter. In this situation, the catheter would only include the centering balloon which would be inflated during the time the radiation source or sources are maneuvered to the treatment site as well as during the treatment period. After a predetermined period of time, the centering balloon is deflated and the catheter, guide wire and radiation source are removed from the body.

BRIEF DESCRIPTION OF THE DRAWINGS

The above and other objects, features and advantages of the present invention will become apparent from the following description and the appended claims, taken in conjunction with the accompanying drawings, in which:

FIG. 1 is a longitudinal sectional view of the balloon catheter passing over a guide wire wherein the guide wire passes through a lumen inside the wall of the catheter;

FIG. 2 is a longitudinal sectional view of the balloon catheter passing over a guide wire wherein the guide wire passes through an opening in the wall of the catheter and runs along the outside of the catheter;

DETAILED DESCRIPTION OF THE PREFERRED EMBODIMENTS

Figure 3:
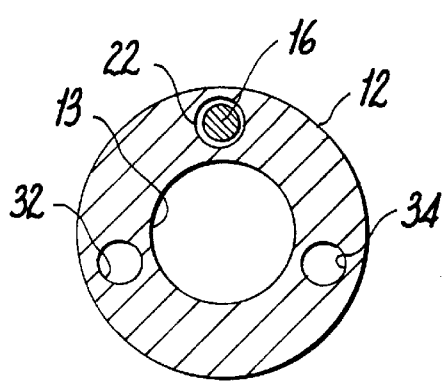
FIG. 3 is a cross-sectional view of FIG. 1 showing the guide wire lumen and two inflation lumens inside the wall of the catheter and an inner treatment lumen of the catheter.

Although the present invention can be used to treat blockages, occlusion or constriction in many body conduits as well as narrow tortuous passageways, for ease of explanation, the present invention will be discussed with respect to a stenosis provided in a blood vessel. Additionally, also for ease of explanation, the same reference numeral would be used for like features.

Referring to FIG. 1 and FIG. 2, the catheter system 10 of the present invention includes a flexible, elongated catheter 12 having a relatively large hollow treatment lumen 13 running the majority of the length of the catheter. An elongated, flexible guide wire 16 is to be used to insure that the catheter 12 is maneuvered to the proper location to treat the stenosis. In the embodiment shown in FIG. 1, a guide wire lumen 22 is provided adjacent to one of the surfaces of the treatment lumen 13. The second embodiment shown in FIG. 2 shows the guide wire 16 passing on the outside of catheter. The guide wire 16 would enter the interior of the catheter by passing through an opening 19 provided at the termination of the distal end of the catheter. The guide wire then passes through slot 24 close to the distal end 15 of the catheter and runs along the outside surface of the treatment lumen 13. The distal end of the catheter end 15 is tapered at 18 to allow ease of maneuverability of the catheter through the narrow conduit or passageway.

The catheter according to the present invention would be used to reduce the size of any stenosis by inflating and deflating a dilatation balloon 14 affixed to the outside surface of the catheter. Radiopaque markings (not shown) are provided on the exterior surface of the catheter at approximately the beginning and the end of the location of the balloon or balloons. The present invention could also utilize one or more centering balloons, the purpose of which will be described hereinbelow. Furthermore, it is noted that it would be possible to utilize this catheter with only the centering balloon or balloons and not employ the dilatation balloon 14 if the stenosis would not be reduced by inflating and deflating the dilatation balloon.

Once the catheter is maneuvered to the treatment site, a radiation source or sources 28 would be maneuvered through the treatment lumen 13 utilizing a guide type wire 30 containing the radiation source or sources. It is noted that if a stenosis must be reduced, the dilatation balloon 14 would be inflated and deflated a number of times. Once the stenosis is reduced, the dilutation balloon is deflated completely and the centering balloon or balloons would be inflated. At this point, the radiation source or sources 28 would be maneuvered to the treatment site utilizing the radiopaque markings. Various types of radiation sources known in the art could be utilized with this treatment. Typical of these radiation sources would be cesium 137, cobalt 60, iodine 125, iodine 131, cobalt 57, iridium 192, gold 198, palladium 103, strontium 89, strontium 90, phosphate 32 or yttrium 90. A solid plug 26 is provided in a distal end of a catheter at the point where the catheter begins to taper to insure that the radiation source 28 remains within the interior of the catheter, and that contamination or germs provided within the treatment lumen 13 do not mix with bodily fluids provided within the passageway.

Figure 5:
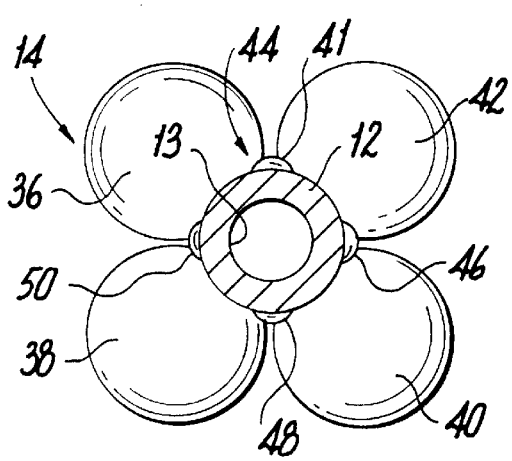
FIG. 5 is transverse cross-sectional view of an inflated multi-lobed dilatation balloon catheter.

FIGS. 5–8 show a multi-lobed centering balloon as well as a multi-lobed dilatation balloon in various states of inflation or deflation. More specifically, FIG. 5 shows the dilatation balloon 14 provided with its four lobes 36, 38, 40 and 42 in the inflated state. As shown in FIG. 1 and FIG. 2, this balloon is attached to the exterior surface of the catheter 12. FIG. 5 also shows a multi-lobed centering balloon 41 having four lobes 44, 46, 48 and 50 in its deflated state. It should be noted that the exact number of lobes of both the dilatation balloon 14 and the centering balloon 41 are not crucial. For that matter, it is noted that the dilatation balloon 14 can be constructed without any lobes. In this situation, the inflation of the dilatation balloon 14 to reduce the size of the stenosis would thereby prevent the perfusion of bodily fluids during the time when this balloon is in its inflated state.

Figure 7:
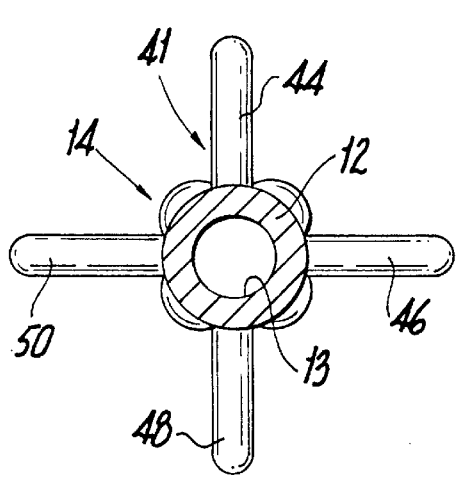
FIG. 7 is transverse cross-sectional view of an inflated multi-lobed centering balloon catheter.
Figure 8:
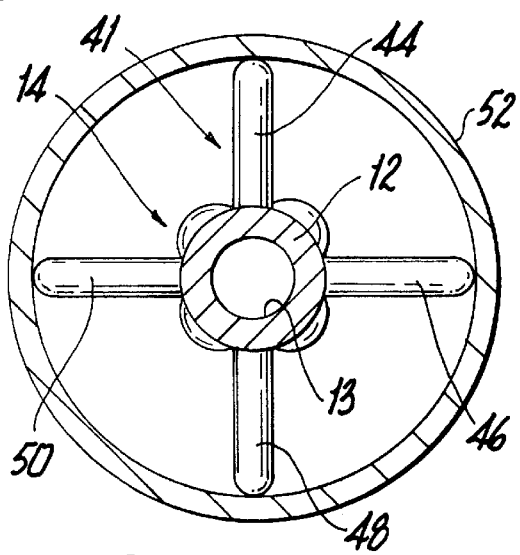
FIG. 8 is transverse cross-sectional view of an inflated multi-lobed centering balloon catheter surrounded by a flexible sheath member.

FIG. 7 and FIG. 8 show the dilatation balloon 14 in its deflated state, and the centering balloon 41 in its inflated state. As can be shown, the lobes 44, 46, 48 and 50 of the centering balloon 41 are relatively thin in volume and would extend symmetrically from the surface of the catheter 12 as a plurality of radiating spokes or thin longitudinal lobes until it abuts the inner surface of the passageway. When the dilatation balloon 14 is inflated, it would fill approximately 90–100% of the passageway thus allowing for little, if any, bodily fluids to perfuse by. When the dilatation balloon 14 is deflated and the centering balloon 41 is inflated, only approximately 30–50% of the passageway would be blocked, thus allowing for bodily fluids to easily perfuse by. Both the dilatation balloon 14 and the centering balloon 41 would be manufactured from materials standard in the industry. This would also be true for the guide wire 16 as well as the catheter 12.

Figure 6:
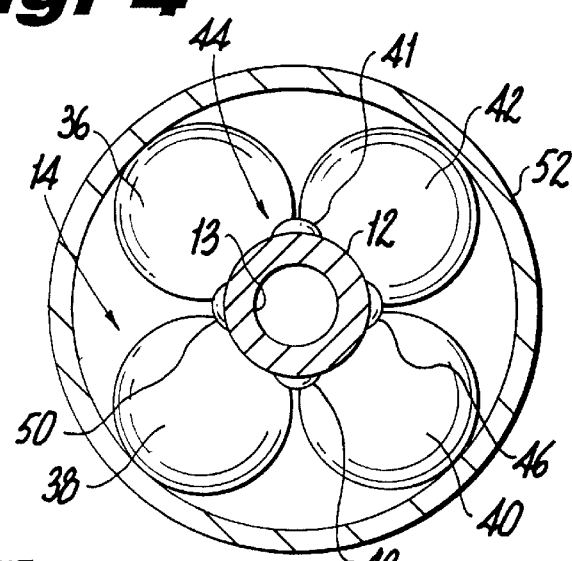
FIG. 6 is transverse cross-sectional view of an inflated multi-lobed dilatation balloon catheter surrounded by a flexible sheath member.

FIG. 6 and FIG. 8 illustrate the utilization of a membrane or sheath 52 which is used to achieve greater dilatation affect while allowing for a better blood perfusion and the centering of the treatment source. Since plaque or other bodily material can plug the perfusion channel or channels between adjacent lobes of the dilatation balloon 14, it is important that the channels between each of the lobes remain free of this material to allow bodily fluid, such as blood, to pass freely between these channels. This is especially true during an angioplasty procedure.

The present invention would overcome this problem by employing the membrane or sheath 52 which would surround the entire ribbed balloon. This membrane or sheath 52 would extend for either the entire length of the balloon 14 or for a portion of the length of the balloon 14. Once the balloon 14 is inflated, the membrane or sheath would be pulled tight between the gaps of the balloon lobes, as the lobes are inflated.

This particular configuration would result in a greater dilatation affect since plaque or other bodily material cannot enter the gap spaces and is forced to move away from the membrane and lobes as expansion takes place due to the inflation of the balloon lobes. Additionally, a perfusion channel or channels is maintained open and bodily fluids will flow freely, since no bodily plaque material can enter the gap spaces to plug or create a damming affect.

The membrane can be constructed from a non-elastic or non-stretching type of material such that a thick overall diameter is achieved when the balloon lobes are inflated. Alternatively, the membrane can also be constructed out of an elastic or stretching type of material so that when the balloon lobes are deflated, the membrane will recoil to its original shape and it is guaranteed that the balloon lobes will compress to as small of a diameter as possible around the catheter 12. This compression would allow for the balloon catheter when it is in its deflated state to pass through tiny constricted spaces. A stretchable membrane also allows for a thick diameter as long as the membrane cannot be stretched beyond the desired diameter of the inflated lobes.

Alternatively, although not specifically illustrated in the drawings, it is noted that the membrane or sheath 52 need not surround the entire surface area of the lobes but can be provided merely between the lobes. Similar to the previously described embodiment, this membrane can be constructed from a non-elastic or an elastic material. Furthermore, this membrane portion may cover the entire length of the balloon 14 or a portion of the length of the balloon 14.

Furthermore, the membrane or sheath 52 would be attached to either the dilatation balloon 14 or the centering balloon 41.

Figure 4:
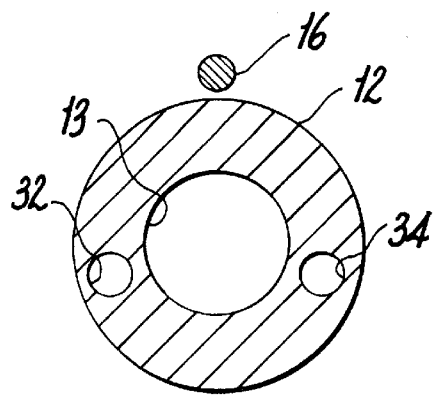
FIG. 4 is a cross-sectional view of FIG. 2 showing the guide wire on the outside of the catheter, two inflation lumens inside the wall of the catheter and an inner treatment lumen of the catheter.

Referring back to FIG. 1 and FIG. 2 as well as FIG. 3 and FIG. 4, the dilatation balloon 14 can be inflated or deflated through the use of a balloon inflation port 56. A lumen 32 within the catheter 12 connected to the balloon 14 and the port 56 is used for this purpose. The centering balloon 41 can be inflated utilizing balloon inflation port 54. A lumen 34 provided within the catheter 12 connected to the balloon 41 and the port 54 is used for this purpose. FIG. 3 is a partial cross-sectional view of the catheter illustrated with respect to FIG. 1 also showing the use of an internal lumen 22 for the guide wire 16. FIG. 4 is a partial cross-sectional view of the catheter shown in FIG. 2 in which the guide wire 16 extends for a portion along the exterior surface of the catheter 12.

Figure 9:
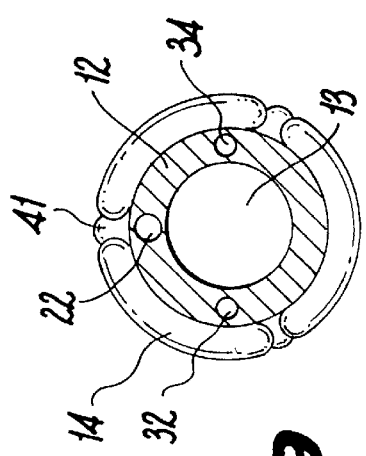
FIG. 9 is a cross-sectional view showing a three-lobe deflated centering balloon and a three-lobe deflated dilatation balloon each attached about the same area to a catheter.

FIG. 9 shows an embodiment in which a three-sided multi-lobed dilatation balloon 14 is provided along the majority of the surface of the catheter 12. Spaces between each of the lobes would allow the various spokes 42 or lobes 41 of the centering balloon to pass therebetween. In this instance, the spokes 42 or lobes 41 of the centering balloon would be attached directly to the exterior surface of the catheter 12.

Figure 10:
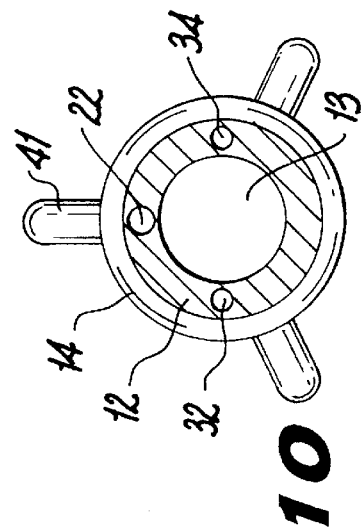
FIG. 10 is a cross-sectional view showing an inflated three-lobe centering balloon attached to a deflated dilatation balloon that is attached to a catheter.

FIG. 10 shows an embodiment in which a non-lobed dilatation balloon 14 is attached to the exterior surface of the catheter 12. As illustrated in FIG. 10, the balloon 14 is in its deflated state. The centering balloon 41 is shown in its inflated state in FIG. 10 and is attached to the exterior surface of the non-lobed balloon 14.

Figure 11:
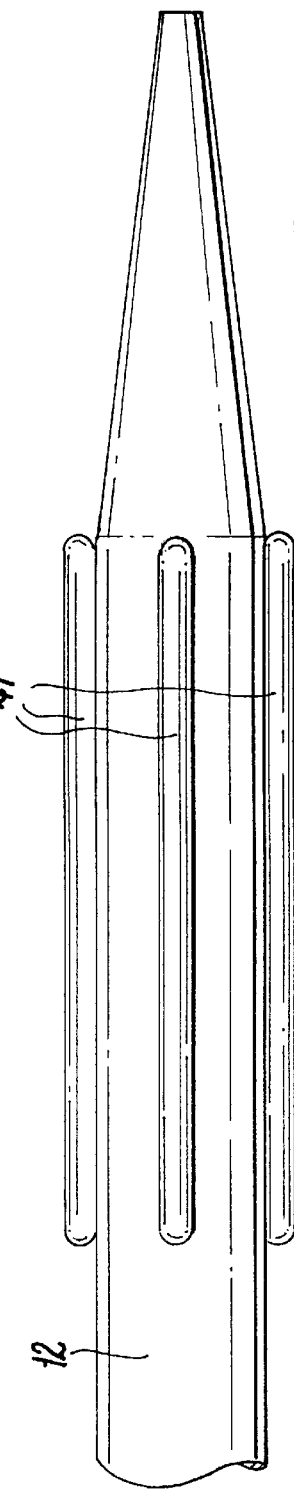
FIG. 11 is a longitudinal view of a multi-lobe longitudinal centering balloons.

FIG. 11 shows a multi-lobe longitudinal centering balloon system which contains a plurality of centering balloons 41, which extend longitudinally along the surface of the catheter.

Figure 12:
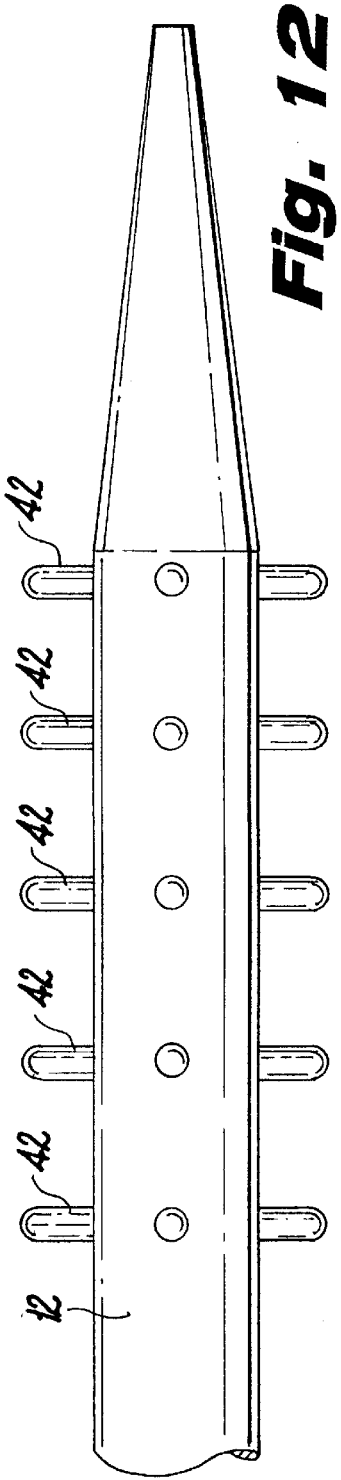
FIG. 12 is a longitudinal view of multi-lobe segmented centering balloons.

FIG. 12 shows a multi-lobe segmented centering balloon system which contains a plurality of sets of centering balloons 42. This embodiment would allow for the maximum perfusion possible.

Although the present invention has been described with reference to specific details of certain embodiments thereof, it is not intended that such details should be regarded as limitations upon the scope of the invention except as and to the extent that they are included in the accompanying claims.

What is claimed is:

1. A device for treating an occlusion or a constriction in a bodily conduit passageway having an inner surface in the body, comprising:
   a flexible, elongated catheter having a distal end and a proximal end, said catheter provided with a first hollow treatment lumen extending within said catheter and provided with an exterior surface;
   a centering balloon attached to said exterior surface proximate to said distal end of said catheter, said centering balloon provided with at least two inflatable thin spokes which are dimensioned and configured to extend from said exterior surface of said catheter to the inner surface of the passageway when said centering balloon is inflated, said spokes encircling said distal end around a first particular point, said at least two inflatable thin spokes surrounded by a flexible membrane attached to said centering balloon; and
   a source for inflating and deflating said centering balloon in communication with said centering balloon;
   wherein when inflated, said centering balloon would allow a significant amount of perfusion of bodily fluids around said spokes.

2. The device in accordance with claim 1, wherein said flexible membrane abuts the inner surface of the passageway to ensure a greater flow of bodily fluids past the occlusion or constriction when said centering balloon is inflated.

3. The device in accordance with claim 2, wherein said centering balloon includes at least one additional set of inflatable thin spokes encircling a portion of said outer surface of said catheter, each of said additional sets of inflatable thin spokes encircling said outer surface at a point removed from said first particular point, each of said thin spokes of a particular set of thin spokes symmetrically spaced from one another.

4. The device in accordance with claim 1, further including a source of radiation maneuvered to the occlusion or constriction through said hollow treatment lumen.

5. The device in accordance with claim 4 further including a flexible membrane attached to said centering balloon, said flexible membrane abutting the inner surface of the passageway to ensure a greater flow of bodily fluids past the occlusion or constriction when said centering balloon is inflated.

6. The device in accordance with claim 5, wherein said centering balloon includes at least one additional set of inflatable thin spokes encircling a portion of said outer surface of said catheter, each of said additional sets of inflatable thin spokes encircling said outer surface at a point removed from said first particular point, each of said thin spokes of a particular set of thin spokes symmetrically spaced from one another.

7. The device in accordance with claim 4 further including a second lumen provided within said catheter connected to said centering balloon and said source for inflating and deflating said centering balloon.

8. The device in accordance with claim 7 further including a flexible, elongated guide wire maneuvered to the occlusion or constriction and a third lumen provided within at least a portion of said catheter within which said guide wire will travel.

9. The device in accordance with claim 8 further including a sealing means provided within said distal end of said catheter for preventing contamination or germs inside of said first lumen from coming into contact with bodily fluids.

10. The device in accordance with claim 8 wherein the termination of said distal end is tapered.

11. The device in accordance with claim 4, wherein said source of radiation is cesium 137, cobalt 60, iodine 125, iodine 131, cobalt 57, iridium 192, gold 198, palladium 103, strontium 89, strontium 90, phosphate 32 or yttrium 90.

12. The device in accordance with claim 1, wherein said centering balloon includes at least one additional set of inflatable thin spokes encircling a portion of said outer surface of said catheter, each of said additional sets of inflatable thin spokes encircling said outer surface at a point removed from said first particular point, each of said thin spokes of a particular set of thin spokes symmetrically spaced from one another.

13. The device in accordance with claim 1 further including a second lumen provided within said catheter connected to said centering balloon and said source for inflating and deflating said centering balloon.

14. The device in accordance with claim 13 further including a flexible, elongated guide wire maneuvered to the occlusion or constriction and a third lumen provided within at least a portion of said catheter within which said guide wire will travel.

15. The device in accordance with claim 14 further including a sealing means provided within said distal end of said catheter for preventing contamination or germs inside of said first lumen from coming into contact with bodily fluids.

16. The device in accordance with claim 14 wherein the termination of said distal end is tapered.

17. The device in accordance with claim 1 wherein each of said spokes are equally spaced from one another around said first particular point.

18. A device for treating an occlusion or a constriction in a bodily conduit passageway having an inner surface in the body, comprising:
   a flexible, elongated catheter having a distal end and a proximal end, said catheter provided with a first hollow treatment lumen extending within said catheter and provided with an exterior surface;
   a dilatation balloon attached to and encircling a portion of said distal end of said catheter;
   a centering balloon attached to a portion of said exterior surface of said distal end of said catheter;

a first source for inflating and deflating said dilatation balloon for the purpose of treating the occlusion or constriction; and a second source for inflating and deflating said centering balloon for the purpose of centering said catheter within the passageway during treatment of the occlusion or constriction, said centering balloon when inflated allowing a significant amount of perfusion of bodily fluids around said centering balloon.

19. The device in accordance with claim 18, wherein said dilatation balloon is provided with a plurality of longitudinally extending lobes whose distance from said exterior surface of said catheter would be relatively constant when said dilatation balloon is inflated.

20. The device in accordance with claim 19, wherein said centering balloon is provided with at least two inflatable thin spokes which would extend from said exterior surface of said catheter to the inner surface of the passageway when said centering balloon is inflated, said spokes encircling said distal end around a first particular point, said centering balloon allowing a significantly greater amount of perfusion of bodily fluids around said spokes than when said centering balloon is deflated and said dilatation balloon is inflated.

21. The device in accordance with claim 20, wherein each of said spokes is equally spaced from one another around said first particular point.

22. The device in accordance with claim 19, wherein said centering balloon is provided with at least two inflatable longitudinal balloons which extend along the exterior surface of said catheter when said centering balloon is inflated, said centering balloon allowing a significantly greater amount of perfusion of bodily fluids around said centering balloon when said centering balloon is deflated and said dilatation balloon is inflated.

23. The device in accordance with claim 18, wherein said centering balloon is provided with at least two inflatable thin spokes which would extend from said exterior surface of said catheter to the inner surface of the passageway when said centering balloon is inflated, said spokes encircling said distal end around a first particular point, said centering balloon allowing a significantly greater amount of perfusion of bodily fluids around said spokes than when said centering balloon is deflated and said dilatation balloon is inflated.

24. The device in accordance with claim 18, wherein said centering balloon is provided with at least two inflatable thin spokes which would extend from said dilatation balloon to the inner surface of the passageway when said centering balloon is inflated, said spokes encircling said distal end around a first particular point, said centering balloon allowing a significantly greater amount of perfusion of bodily fluids around said spokes than when said centering balloon is deflated and said dilatation balloon is inflated.

25. The device in accordance with claim 18, further including a source of radiation maneuvered to the occlusion or constriction through said hollow treatment lumen.

26. The device in accordance with claim 25 further including a flexible member attached to said centering balloon, said flexible membrane abutting the inner surface of the passage-way to ensure a greater flow of bodily fluids past the occlusion or constriction when said centering balloon is inflated.

27. The device in accordance with claim 25 further including a flexible membrane attached to said dilatation balloon, said flexible membrane abutting the inner surface of the passageway to ensure a greater flow of bodily fluids past the occlusion or constriction when said dilatation balloon is inflated.

28. The device in accordance with claim 25 wherein said centering balloon includes at least one additional set of inflatable thin spokes encircling a portion of said outer surface of said catheter, each of said additional sets of inflatable thin spokes encircling said outer surface at a point removed from said first particular point, each of said thin spokes of a particular set of thin spokes symmetrically spaced from one another.

29. The device in accordance with claim 25, further including a second lumen provided with said catheter connected to said dilatation balloon and said first source for inflating and deflating said dilatation balloon.

30. The device in accordance with claim 29, further including a third lumen provided within said catheter connected to said centering balloon and said second source for inflating and deflating said centering balloon.

31. The device in accordance with claim 30 further including a flexible, elongated guide wire maneuvered to the occlusion or constriction and a fourth lumen provided within at least a portion of said catheter within which said guide wire will travel.

32. The device in accordance with claim 31 wherein the termination of said distal end is tapered.

33. The device in accordance with claim 25, wherein said source of radiation is cesium 137, cobalt 60, iodine 125, iodine 131, cobalt 57, iridium 192, gold 198, palladium 103, strontium 89, strontium 90, phosphate 32 or yttrium 90.

34. The device in accordance with claim 18 further including a flexible member attached to said centering balloon, said flexible membrane abutting the inner surface of the passage-way to ensure a greater flow of bodily fluids past the occlusion or constriction when said centering balloon is inflated.

35. The device in accordance with claim 18 further including a flexible membrane attached to said dilatation balloon, said flexible membrane abutting the inner surface of the passageway to ensure a greater flow of bodily fluids past the occlusion or constriction when said dilatation balloon is inflated.

36. The device in accordance with claim 18 wherein said centering balloon includes at least one additional set of inflatable thin spokes encircling a portion of said outer surface of said catheter, each of said additional sets of inflatable thin spokes encircling said outer surface at a point removed from said first particular point, each of said thin spokes of a particular set of thin spokes symmetrically spaced from one another.

37. The device in accordance with claim 18, further including a second lumen provided with said catheter connected to said dilatation balloon and said first source for inflating and deflating said dilatation balloon.

38. The device in accordance with claim 37, further including a third lumen provided within said catheter connected to said centering balloon and said second source for inflating and deflating said centering balloon.

39. The device in accordance with claim 38 further including a flexible, elongated guide wire maneuvered to the occlusion or constriction and a fourth lumen provided within at least a portion of said catheter within which said guide wire will travel.

40. The device in accordance with claim 39 further including a sealing means provided within said distal end of said catheter for preventing contamination or germs inside of said first lumen from coming into contact with bodily fluids.

41. The device in accordance with claim 39 wherein the termination of said distal end is tapered.

42. The device in accordance with claim 18, wherein said centering balloon is provided with at least two inflatable longitudinal balloons which extend along the exterior surface of said catheter when said centering balloon is inflated, said centering balloon allowing a significantly greater amount of perfusion of bodily fluids around said centering balloon when said centering balloon is deflated and said dilatation balloon is inflated.

43. The device in accordance with claim 31 further including a sealing means provided within said distal end of said catheter for preventing contamination or germs of said first lumen from coming into contact with bodily fluids.

* * * * *

UNITED STATES PATENT AND TRADEMARK OFFICE
CERTIFICATE OF CORRECTION

PATENT NO. : 5,947,924
DATED : September 7, 1999
INVENTOR(S) : Samuel F. Liprie

It is certified that error appears in the above-identified patent and that said Letters Patent are hereby corrected as shown below:

Column 5, line 19, delete "dilutation" and insert therefor --dilatation--
Column 9, line 21, insert --,when inflated,-- after "balloon"
Column 9, line 43, insert --, when inflated,-- after "balloon"

Signed and Sealed this

Tenth Day of April, 2001

Attest:

NICHOLAS P. GODICI

*Attesting Officer*        *Acting Director of the United States Patent and Trademark Office*